(12) United States Patent
Schneider

(10) Patent No.: US 10,835,213 B2
(45) Date of Patent: Nov. 17, 2020

(54) QUALITY METRIC FOR MULTI-BEAT ECHOCARDIOGRAPHIC ACQUISITIONS FOR IMMEDIATE USER FEEDBACK

(71) Applicant: KONINKLIJKE PHILIPS N.V., Eindhoven (NL)

(72) Inventor: Robert Joseph Schneider, Windham, NH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 321 days.

(21) Appl. No.: 15/508,953

(22) PCT Filed: Aug. 26, 2015

(86) PCT No.: PCT/IB2015/056457
§ 371 (c)(1),
(2) Date: Mar. 6, 2017

(87) PCT Pub. No.: WO2016/038491
PCT Pub. Date: Mar. 17, 2016

(65) Prior Publication Data
US 2017/0273669 A1   Sep. 28, 2017

Related U.S. Application Data

(60) Provisional application No. 62/048,853, filed on Sep. 11, 2014.

(51) Int. Cl.
*A61B 8/08* (2006.01)
*G06T 5/50* (2006.01)
*G06T 7/00* (2017.01)

(52) U.S. Cl.
CPC .......... *A61B 8/5276* (2013.01); *A61B 8/0883* (2013.01); *A61B 8/483* (2013.01);
(Continued)

(58) Field of Classification Search
CPC ....... A61B 8/5269–5292; A61B 5/7285–7289; G06T 7/0012
See application file for complete search history.

(56) References Cited

U.S. PATENT DOCUMENTS 8,879,813 B1 * 11/2014 Solanki .................. G16H 30/20
382/128
10,140,421 B1 * 11/2018 Bernard ................ G06F 19/321
(Continued)

FOREIGN PATENT DOCUMENTS

CN        101491450 A      7/2009

OTHER PUBLICATIONS

Lang, et al., "EAE/ASE Recommendations for Image Acquisition and Display Using Three-Dimensionall Echocardiography", European Heart Journal, Cardiovascular Imaging, vol. 13, No. 1, Jan. 24, 2012, pp. 1-46.

*Primary Examiner* — Jonathan Cwern

(57) ABSTRACT

An imaging system includes an imaging device (10) configured to acquire an image in a multi-beat acquisition mode. A quality scoring module (115) is stored in memory and is configured to evaluate changes in the image between portions of a multi-beat cycle to compute a quality score (136) indicating a suitability of the image. A display (118) is included for viewing the image and displaying the quality score as real-time feedback for the image.

13 Claims, 5 Drawing Sheets

(52) U.S. Cl.
CPC .............. *G06T 5/50* (2013.01); *G06T 7/0012* (2013.01); *A61B 8/5284* (2013.01); *G06T 2207/10132* (2013.01); *G06T 2207/30168* (2013.01)

(56) References Cited

U.S. PATENT DOCUMENTS

| | | |
|---|---|---|
| 2005/0080336 A1 | 4/2005 | Byrd et al. |
| 2005/0251013 A1 | 11/2005 | Krishnan et al. |
| 2009/0187106 A1 | 7/2009 | Lee et al. |
| 2009/0324049 A1* | 12/2009 | Kontos .................. A61B 6/502 382/132 |
| 2011/0110572 A1 | 5/2011 | Guehring et al. |
| 2013/0190600 A1 | 7/2013 | Gupta et al. |
| 2014/0275945 A1* | 9/2014 | Fonte ................... G06T 7/0012 600/407 |
| 2015/0133743 A1* | 5/2015 | Baron ..................... G16H 40/40 600/301 |
| 2015/0327838 A1* | 11/2015 | Francis ................ A61B 8/0883 600/450 |
| 2016/0148373 A1* | 5/2016 | Robinson .............. G06T 7/0012 382/103 |
| 2019/0076127 A1* | 3/2019 | Aase .................... A61B 8/5215 |
| 2019/0125298 A1* | 5/2019 | Abolmaesumi ...... A61B 8/0883 |

\* cited by examiner

QUALITY METRIC FOR MULTI-BEAT ECHOCARDIOGRAPHIC ACQUISITIONS FOR IMMEDIATE USER FEEDBACK

This application is the U.S. National Phase application under 35 U.S.C. § 371 of International Application No. PCT/IB2015/056457, filed on Aug. 26, 2015, which claims the benefit of U.S. Provisional Application Ser. No. 62/048,853, filed Sep. 11, 2014. These applications are hereby incorporated by reference herein.

BACKGROUND

Technical Field

This disclosure relates to medical instruments and more particularly to a metric, system and method for indicating the quality of a multi-beat echocardiographic measurement.

Description of the Related Art

In echocardiography, trade-offs are made between field-of-view (FOV), spatial resolution, and temporal resolution. Typically, if more of one parameter is needed, the other parameters suffer. For example, if a larger FOV is required, the spatial resolution (and image quality) and temporal resolution are likely to be reduced. This trade-off may be circumvented in echocardiography, especially for 3D volume acquisitions, by using electrocardiograph (ECG)-gated multi-beat acquisitions. These acquisitions exploit the periodicity of cardiac motion to construct large FOV images that have both higher spatial and temporal resolution than could otherwise be obtained if the same FOV was obtained in a single cycle.

A multi-beat acquisition typically operates by acquiring only a portion, or segment, of the FOV in any given cycle, where timing of the acquisition is driven from the ECG waveform, specifically the R-peak. The mode then stitches the multiple segments into a single image once the acquisition is complete. This can be seen in the 2Q, 4Q, and 6Q acquisition modes (herein referred to as the NQ acquisition mode) on an ultrasound system (e.g., the Philips® EPIQ™ system). Another multi-beat acquisition mode called "HVR" mode operates in a slightly different fashion in that it acquires a sparse subset of scan lines throughout the entire FOV in any given cardiac cycle. The remaining set of scan lines in the FOV are acquired in subsequent cardiac cycles in similar sparse patterns. At any given time, an image is formed from the acquired set of scan lines for a given frame or an interpolation of the scan lines should the image content from one beat to another not appear to line up correctly.

One problem with multi-beat acquisitions is that they rely on the assumption that the heart and probe are in the same position during the succession of cardiac cycles. However, often the heart or probe will be in slightly different locations during different beats due to either movement of the probe by the clinician, movement of the patient, movement of the heart due to respiration, or beat-to-beat variability. These movements manifest as stitch artifacts in the final image sequence for the case of NQ image modes, or in the case of the HVR mode, a lower image quality (IQ) due to the fact that interpolation will then be used to fill out the volume as opposed to actually acquired scan lines. These occurrences can be subtle, but can lead to variability and inaccuracies in quantification of the image. Currently, the clinician detects when such an acquisition contains these artifacts or lower IQ, and decides, based on the severity, whether or not to acquire another image. As the artifacts or lower IQ are not immediately visible, due to the 3D nature of the images and due to their subtle nature, accurate detection can be time consuming and can require a great deal of skill.

SUMMARY

In accordance with the present principles, an imaging system includes an imaging device configured to acquire an image in a multi-beat acquisition mode. A quality scoring module is stored in memory and is configured to evaluate changes in the image between portions of a multi-beat cycle to compute a quality score indicating a suitability of the image. A display is provided for viewing the image and displaying the quality score as real-time feedback for the image.

Another imaging system includes an ultrasound imaging device configured to acquire an image in an electrocardiograph multi-beat acquisition mode. A quality scoring module is stored in memory and is configured to evaluate changes in the image between portions of a multi-beat cycle to compute a quality score indicating a suitability of the image. The quality scoring module includes a combination method that combines individual quality scores into an overall quality score. A display is included for viewing the image and displaying the quality score as real-time feedback for the image. An interface is configured to permit acceptance or rejection of the image based on the overall quality score.

An imaging method includes acquiring an image in a multi-beat acquisition mode; quality scoring the image to evaluate changes in the image between portions of a multi-beat cycle to compute a quality score indicating a suitability of the image; and displaying the image and the quality score as real-time feedback for the image.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
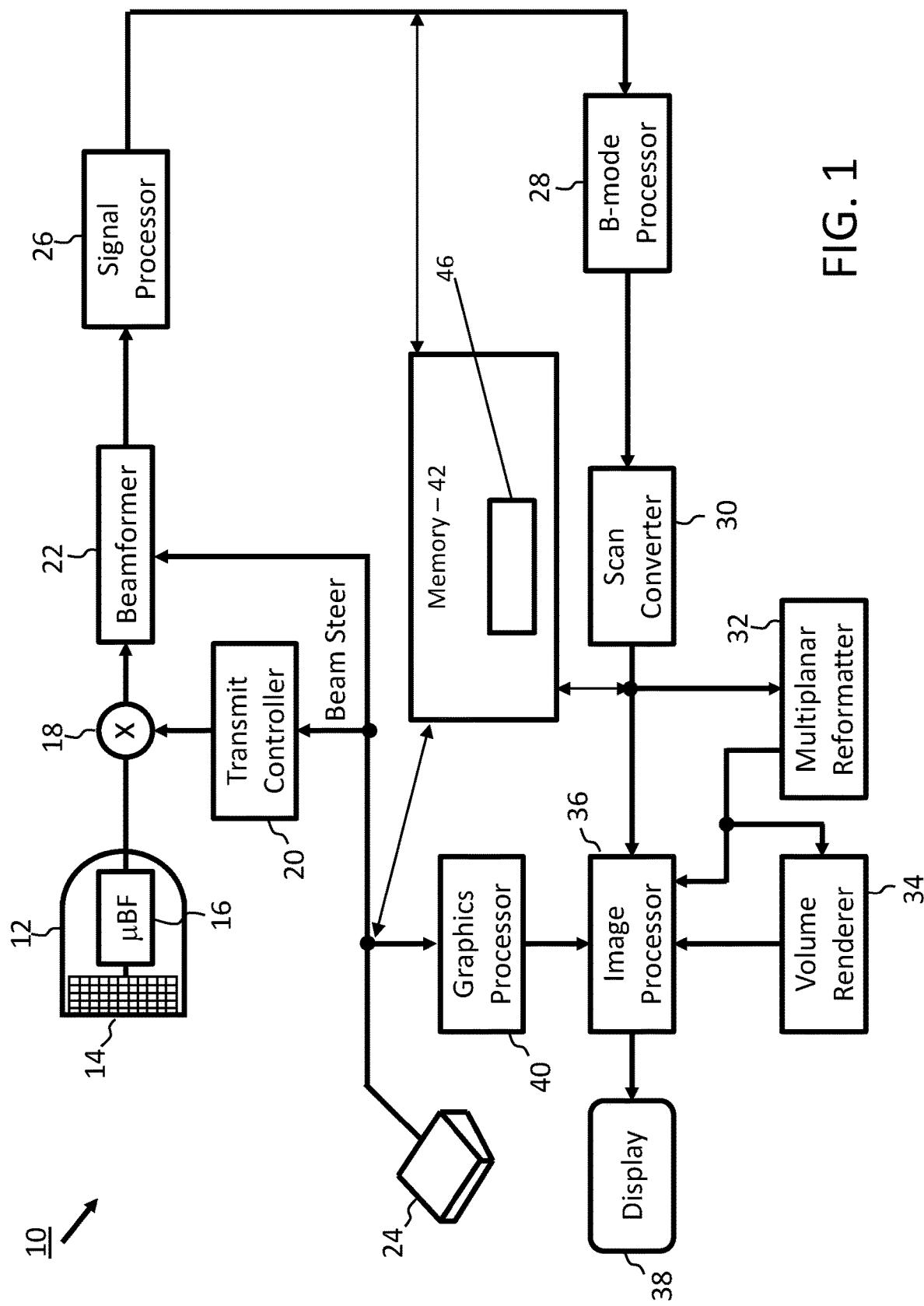
FIG. 1 is a block/flow diagram showing an ultrasonic imaging system providing a quality metric for evaluating an image in accordance with one embodiment.

In accordance with the present principles, an automated and immediate quality score for multi-beat acquisitions is provided, which can be employed by a clinician to assess the quality of an acquisition and a subsequent value of the image for quantification. The quality can be derived from a number of sources, such as, e.g., from an image-based analysis, from analysis of the ECG waveform (which is used for the gating process for the acquisition), from probe motion detected either through image-based motion estimations, from sensor-based (i.e., electromagnetic, optical, or accelerometer sensors) estimations, etc.

Conventionally, it is up to a clinician performing a scan to assess the quality, or lack thereof, of a multi-beat acquisition based on what the clinician can observe in the image after the acquisition. Detecting artifacts in the case of an NQ imaging mode or lower image quality in the case of the HVR mode is often difficult. In the case of an NQ imaging mode, the user needs to know how the image was formed (i.e., by acquiring multiple contiguous segments which are then stitched together after all cardiac cycles have been obtained). With this information, the user then needs to know where to look for stitching artifacts. Locations of stitching artifacts can change depending on how many cycles were used during the acquisition. Even so, the stitching artifact may not be immediately obvious during the scanning session and may not be noticed until offline visual inspection or quantification. At offline visual inspection or quantification, if it is decided that the image is unsuitable (for example, for quantification purposes) it is already too late to re-acquire another image.

In the case of an HVR acquisition, the user needs to know that at any given time the image can be made up of actually acquired scan lines or an interpolation of scan lines should it be found that data acquired in successive cardiac cycles does not align. If the user is unaware of this fact, they may acquire an image not knowing that a higher quality image is forthcoming if they were to wait a little longer, hold the probe steadier or ask the patient to limit their movement and/or respiration, thereby allowing the interpolated regions to be filled-in or acquired in subsequent cycles.

These multi-beat acquisitions typically take place within the context of 3D image acquisition, which can further complicate issues. Acquiring 3D images, understanding how to interpret the images and knowing how to navigate around the images requires significant training. Knowing how and when to also interpret multi-beat acquisitions and when to accept or reject these acquisitions are added complications. An ultrasound machine has sufficient information about the multi-beat acquisition mode and the image formation process to be able to detect artifacts or low IQ automatically. In accordance with the present principles, by providing a quality metric (or metrics) to give immediate feedback to the user as to the quality of the image, less time and expertise are needed on the part of the scanning clinician to accept or reject the image. Guidance can also be provided to assist the user in how to correct the acquisition, and ultimately encourage 3D image adoption by novice users.

The quality metric may be computed on a multi-beat acquisition to provide immediate feedback to the clinician performing the scanning as to the quality of the acquisition. Multi-beat acquisitions have a high potential for variability and image artifacts, namely stitch artifacts, and these can be subtle and not always immediately visible by the clinician. Since the variability and artifacts can cause confusion and inaccuracies both in observation of the image and in quantification, a determination as to when these occur and their severity need to be made. Since multi-beat acquisitions typically take place within the context of a 3D image acquisition, and since navigating around and comprehending 3D images can be difficult, especially for novice 3D users, the present principles aim to make the adoption of 3D imaging easier on clinicians by providing an immediate and easy to understand quality metric that will help them decide whether or not to acquire a new multi-beat acquisition.

A quality metric in accordance with the present principles may be derived from one or more sources or a combination of sources. One source may include image content around stitch locations within an image relative to the image content not at stitch locations. A low quality might be found if the content around the stitch location had noticeably different characteristics than in the rest of the image. Another source may include an ECG waveform, where beat-to-beat irregularities in the electrophysiology would indicate a lower quality acquisition as the heart likely would not be in the same position during every cycle during the acquisition. Another source may include motion sensors (such as, e.g., image-based motion detection, electromagnetic sensors, optical sensors, accelerometers, etc.), which can detect movements of the probe that could cause variability and lower the quality of the image. Other sources may also be employed.

It should be understood that the present invention will be described in terms of medical instruments; however, the teachings of the present invention are much broader and are applicable to any instruments capable of combining information into a quality metric. In some embodiments, the present principles are employed in tracking or analyzing complex biological or mechanical systems. In particular, the present principles are applicable to internal tracking procedures of biological systems, procedures in all areas of the body such as the lungs, heart, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, an ultrasound imaging system 10 constructed in accordance with the present principles is shown in block diagram form.

In the ultrasonic diagnostic imaging system of FIG. 1, the ultrasound imaging system 10 includes a probe 12 having a transducer or transducer array 14 for transmitting ultrasonic waves and receiving echo information. A variety of transducer arrays are well known in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. The transducer array 14 is coupled to a microbeamformer 16 in the probe 12, which controls transmission and reception of signals by the transducer elements in the array. In this example, the microbeamformer 16 is coupled by the probe cable to a transmit/receive (T/R) switch 18, which switches between transmission and reception and protects a main beamformer 22 from high energy transmit signals. In some embodiments, the T/R switch 18 and other elements in the system can be included in the transducer probe rather than in a separate ultrasound system base.

The transmission of ultrasonic beams from the transducer array 14 under control of the microbeamformer 16 is directed by a transmit controller 20 coupled to the T/R switch 18 and the main beamformer 22, which may receive input from the user's operation of a user interface or control panel 24.

One function controlled by the transmit controller 20 is the direction in which beams are steered. Beams may be steered straight ahead from (orthogonal to) the transducer array, or at different angles for a wider field of view. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B mode processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.). The 2D or 3D images are coupled from the scan converter 30, multiplanar reformatter 32, and volume renderer 34 to an image processor 36 for further enhancement, buffering and temporary storage for display on an image display 38. A graphics processor 40 can generate graphic overlays for display with the ultrasound images. These graphic overlays or parameter blocks can contain, e.g., standard identifying information such as patient name, date and time of the image, imaging parameters, frame indices and the like. For these purposes, the graphics processor 40 receives input from the user interface 24, such as a typed patient name. The user interface 24 can also be coupled to the multiplanar reformatter 32 for selection and control of a display of multiple multiplanar reformatted (MPR) images.

In accordance with the present principles, ultrasound data is acquired and stored in memory 42 in a format that permits real-time review of multi-beat acquisition data from, e.g., a heart. In one embodiment, a quality scoring application 46 is stored in memory 42 for analyzing image data to output a quality parameter that indicates to the operator the quality of the current data. In one embodiment, the ultrasound imaging system 10 includes a multi-beat acquisition mode, which generates a display for the user on a display 38.

In one embodiment, the ultrasound imaging system 10 is capable of acquiring an apical transthoracic 3D image of the heart from an intercostal window using a 4Q imaging mode with an X5 transducer (e.g., as in a Philips® EPIQ™ system). Once computed for the acquisition, a final quality score may be displayed on the display 38 along with the image, and also saved with the image file for offline display. The memory 42 is depicted as being placed after the scan converter 30; however, the memory 42 may store data and interact at any position in the signal path.

Figure 2:
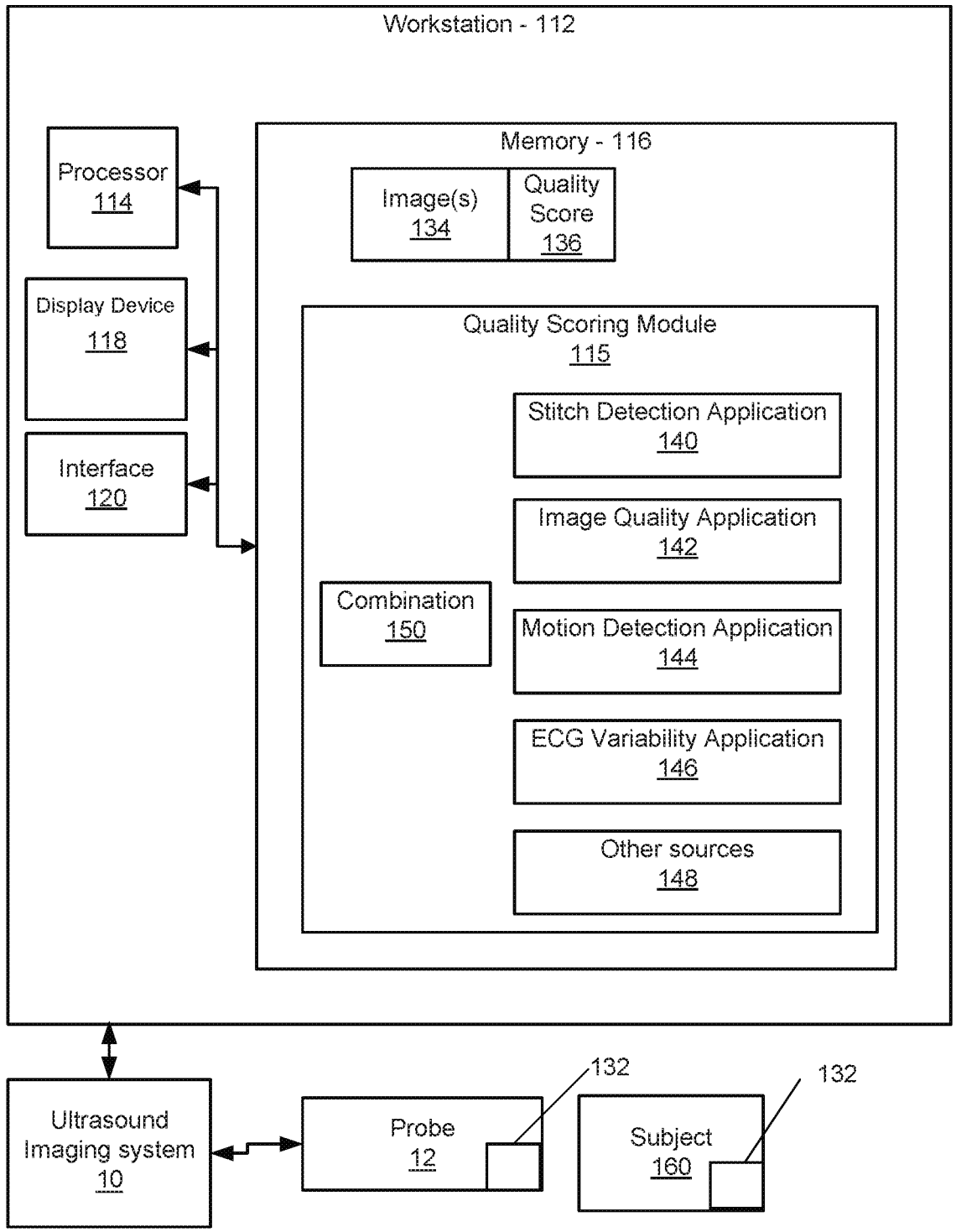
FIG. 2 is a block/flow diagram showing an ultrasonic imaging system showing a quality scoring module for evaluating an image in greater detail in accordance with another embodiment.

Referring to FIG. 2, a system 100 for review of ultrasound images is illustratively shown in accordance with one embodiment. System 100 may include a workstation or console 112 from which images are reviewed and modes selected. System 100 may be incorporated into or function in conjunction with an imaging system (e.g., ultrasound imaging system 10) or may be a separate unit or module. Workstation 112 preferably includes one or more processors 114 and memory 116 for storing programs, applications and data. Memory 116 may store a quality scoring module 115 configured to collect acquired data and compute a real-time quality score for acquired images.

The quality scoring module 115 is configured to receive image data and evaluate data from one or more sources (e.g., different imaging parameters or data content). An image 134 can be generated that includes the image (e.g., a multi-beat 3D acquisition image) and a quality score 136, which can be displayed on a display device 118. The image and the score may be stored together (or separately) in memory 116. Workstation 112 includes the display device 118 for reviewing internal images of a subject (e.g., a patient, a heart in the patient, etc.). Display device 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

A real-time quality metric(s) or score(s) 136 that are displayed to the user during any multi-beat acquisition mode indicate to the user the quality, or lack thereof, of the multi-beat acquisition. Quality scores 136 are computed from a number of different sources (e.g., from images 134 or even external measurements, e.g., sensors). The sources may include those listed herein as well as other sources. The quality score(s) 136 should be shown to the user during the acquisition process, but may also be saved with the image 134 (e.g., in the Digital Imaging and Communications in Medicine (DICOM) file).

Some illustrative sources will be described in accordance with illustrative embodiments. The sources described herein are not exhaustive and additional sources may be provided instead of or in addition to those described. In addition, the sources may be combined in various combinations by a combination method or module 150. One or more sources may be employed in computing the quality metric(s) 136.

One source may include a stitch detection application 140 (for NQ image modes). The stitch detection application 140 employs regions of the image at stitch locations that are compared to regions of the image not at stitch locations. Low scores would be generated if large gradients were found at the stitch region as compared to other regions, indicating a stitch artifact.

Another source may include an image quality (IQ) detection application 142 (e.g., for HVR image modes). As the image is made up of either actually acquired scan line data or interpolated scan line data, the quality metric 136 computed can be proportional to the amount of the volume that is made up of actually acquired scan line data. A perfect (high) score in this regard would indicate the entire volume is made up of actually acquired scan line data. A low score would indicate that the image is computed from the least number of actually acquired scan lines possible to form an image.

A motion detection application 144 may also be included. Since multi-beat acquisitions rely on the assumption that the probe and heart will be in the same position and orientation in a succession of cardiac cycles, if motion is detected between cardiac cycles, the image should be given a lower quality score versus if no motion is detected. Motion can be detected from a number of different sources. Image-based motion detection could be computed using methods similar to those employed in the HVR mode, or by performing spatial registration of overlapping image segments. Motion can also be detected from motion sensors 132. For example, the motion sensors 132 may include electromagnetic sensors, optical sensors, or accelerometers placed in or around probe 12 for the ultrasound imaging system 10 and could measure motion of the probe 12 during an acquisition. The more motion that occurs during the acquisition, the lower the quality score. The relative motion of a subject 160 or other objects may also be monitored using motion sensors 132.

An ECG variability application 146 may be employed. Multi-beat acquisitions usually employ ECG-gating to temporally align image data acquired in successive cardiac cycles. If beat-to-beat variability occurs, then the quality of the multi-beat acquisition is likely to suffer. Therefore, several ECG waveforms and/or detected temporal landmarks may be employed to compare and temporally align the image data (such as the R-peak) within the multi-beat acquisition. A high variability in the waveforms or temporal landmarks would result in a lower quality score.

Another source 148 may include other image artifacts or external environmental inputs employed to influence the quality score 136. The generation of the quality score 136 may be integrated into a multi-beat acquisition mode and displayed to the user. In one embodiment, an apical transthoracic 3D image of the heart from an intercostal window using the 4Q imaging mode and an X5 transducer may have a quality score 136 generated. Once computed for the acquisition, the final quality score 136 would be displayed on a screen of the display device 118 along with the image, and also saved with the image file for offline display.

Figure 3:
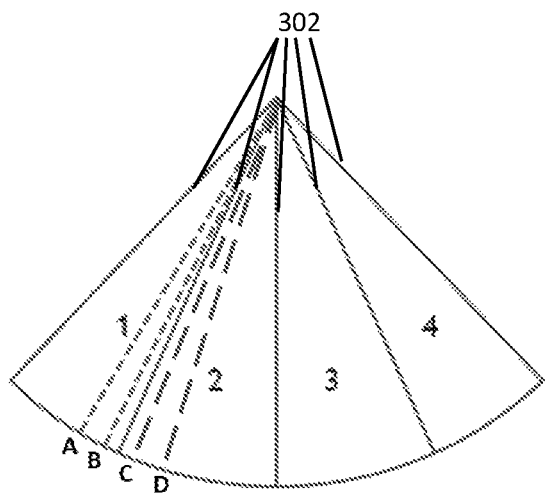
FIG. 3 is a diagram showing stitching locations for computing a stitching quality metric in accordance with one embodiment.

Referring to FIG. 3, a diagram illustratively demonstrates the computation of a stitch score in accordance with one exemplary embodiment. A stitch score may be computed at each stitch location 302 shown in FIG. 3, e.g., between sectors labeled 1-4, i.e., between sectors 1 and 2, sectors 2 and 3 and sectors 3 and 4. The stitch score may be computed by comparing a difference between scan lines near the stitch location 302 but within the same segment (such as A and B or C and D) to the difference between scan lines on either side of the stitch location 302 (such as B and C). If there are M elements along the axial direction, a score could be computed as provided in Eqs. 1. A final stitch score for the volume would range between 0 and 1, with 1 being the highest quality score.

$$S_{stitch1\text{-}2} = \frac{1}{M} \sum_{m=1}^{M} ||A_m - B_m| - |B_m - C_m|| \qquad (1)$$

$$S_{stitch} = \frac{1}{1 + \max\{S_{stitch1\text{-}2}, S_{stitch2\text{-}3}, S_{stitch_{3\text{-}4}}\}}$$

where $S_{stitch}$ is a stitch score; m is an element index for scan lines; M is the total number of elements; A, B and C are the number of scans lines at the locations A, B or C; and max is the maximum value function.

Figure 4:
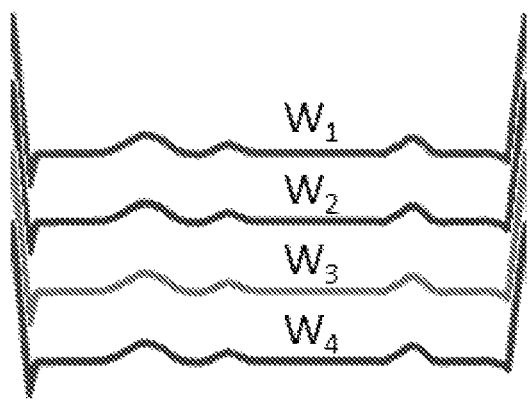
FIG. 4 is a diagram showing waveforms for computing an ECG variability quality metric in accordance with one embodiment.

Referring to FIG. 4, a diagram illustratively demonstrates the computation of an ECG variability score in accordance with one exemplary embodiment. An ECG variability score may be computed by comparing waveforms, e.g., waveforms $W_1$, $W_2$, $W_3$ and $W_4$ from each cardiac cycle during the acquisition. A score $S_{ecg}$ could be computed in accordance with Eq. (2), where there are four traces (t=4) and the first M elements from each trace are compared. Similar to the stitch score, the ECG score would range between 0 and 1, with 1 being the highest quality score.

$$S_{ecg} = \frac{1}{1 + \frac{1}{M} \sum_{m=1}^{M} \max_t \left| W_t(m) - \frac{W_1(m) + W_2(m) + W_3(m) + W_4(m)}{4} \right|} \qquad (2)$$

In one embodiment, each individual quality score may be made to range between 0 and 1, with 1 being the highest quality score. As such, these individual scores could be labeled and displayed to the user in real-time so that the user knows how each component of the image scored, or the scores could be combined into a single score in one of several ways, as will be described, where each final score would also range from 0 to 1, with 1 being the highest quality score.

One combination method to compute the final score may include individual scores as independent variables as in Eq. (3). Another combination method may include individual scores with the individual scores not necessarily being independent as in Eq. (4), where min is the minimum value function.

$$S_{final} = S_{stitch} \times S_{acq} \quad (3)$$

$$S_{final} = \min\{S_{stitch}, S_{ecg}\} \quad (4)$$

Other combination methods may include taking an average, taking a weighted average, adding the quality scores, etc. For example, weightings for each individual quality score may be prioritized based on importance or other criteria to compute the overall quality score from a plurality of sources. The final score may include other individual scores as well. The final score may include a single number between 0 and 1, although other values may be employed.

In one embodiment, an image quality (IQ) score for the HVR mode, and a motion score, when motion detection (from image-based detection or motion sensors) is employed, may include the following. The IQ score and the motion detection score may be shown individually to the user or combined with the other scores into a final score in a similar way as described above in the example.

An HVR image may be computed from scan lines, where the scan lines are either actually acquired or are interpolated from neighboring scan lines. Consider: $N_{total}$ as the total number of scan lines used to compute an image, $N_{min}$ as the minimum number of actually defined scan lines needed to compute an image, and $N_{def}$ as the number of defined scan lines in any given image. Then, an HVR image quality score ($S_{IQ}$) could be computed as in Eq. (5), where the score ranges from 0 to 1, with 1 being the highest quality score.

$$S_{IQ} = \frac{N_{def} - N_{min}}{N_{total} - N_{min}} \quad (5)$$

A motion score may also be determined based on the motion of the probe or anatomical motion. Motion can be detected in a number of ways. For example, motion can be estimated by performing an image-based registration of overlapping segments acquired during the different cardiac cycles. Motion can also be estimated using any number of sensors, such as electromagnetic sensors, optical sensors, accelerometers, etc. These sensors could be placed on the patient, on the probe and/or in the probe to detect motion of the probe or the anatomy being imaged. Depending on the motion sensing method and where the motion sensing is taking place (e.g., on or in the probe and/or on the patient), prior knowledge about the maximum amount of tolerable motion may be employed to determine motion thresholds, $D_{thresh}$. If $X_{ref}$ is the reference position of the probe or patient at some reference stage and $X_m$ is the position of the probe at any given time, where M position samples are taken during the acquisition, then, a motion score ($S_{motion}$) could be computed in accordance with Eq. 6. Scores can range from 0 to 1, with 1 being the highest quality score.

$$S_{motion} = 1 - \frac{\max\{D_{thresh}, \max_m \|X_{ref} - X_m\|\}}{D_{thresh}} \quad (6)$$

Figure 5:
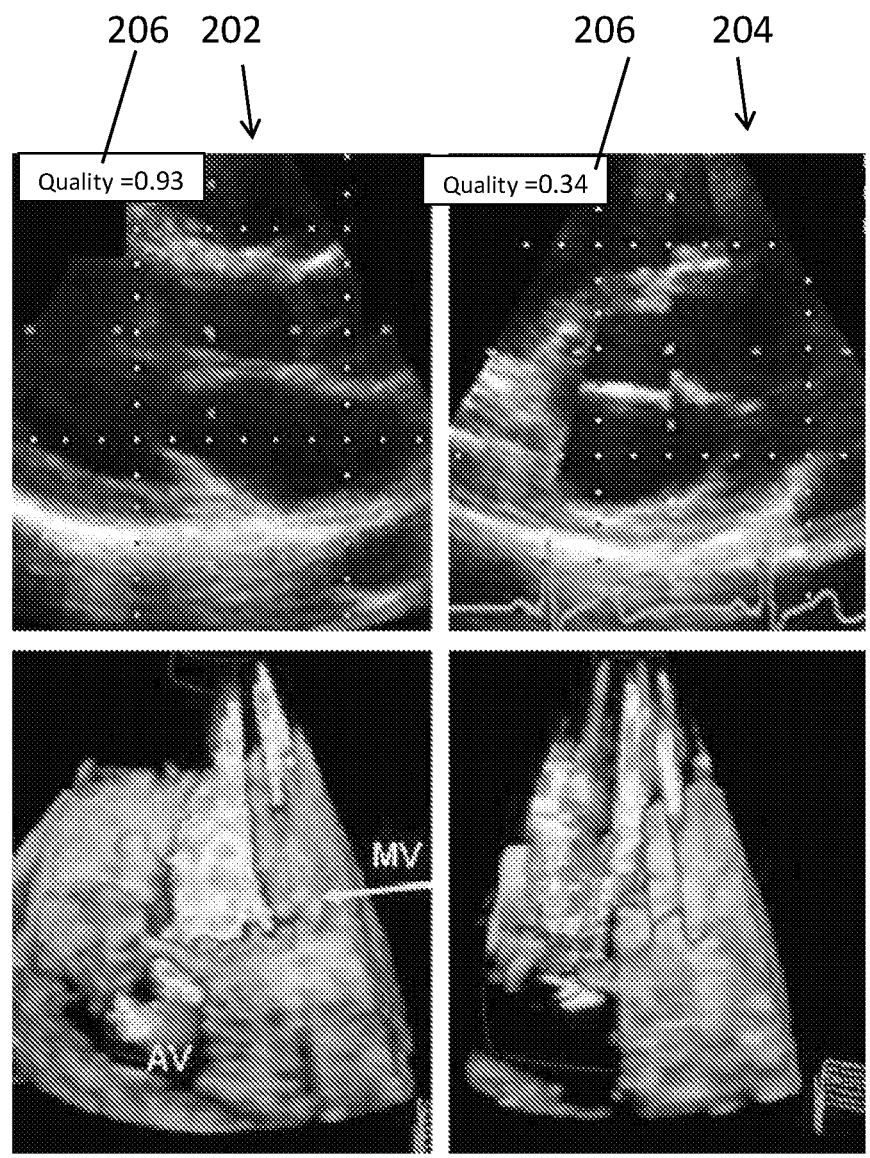
FIG. 5 is an image showing a quality score displayed therein for providing feedback on the image in accordance with one embodiment.

Referring to FIG. 5, an example of a multi-beat acquisition without stitching artifacts 202 and with stitching artifacts 204 is illustratively depicted. The artifacts can be subtle and not so easily detected. Therefore, a quality score 136 appears as an indicator 206 to the user to assess the quality of a multi-beat acquisition based on motion, stitch artifacts, ECG uniformity, image quality, etc. and is designed to guide the user on whether or not to accept the image, use the image for quantification, and/or acquire a new image. The present principles are useful for all ECG-gated multi-beat acquisitions on ultrasound systems. These include, but are not limited to, 2Q, 4Q, 6Q, HVRQ, and HMQ imaging modes. The present principles also apply to ultrasound images acquired on probes with motion sensors (e.g., gyroscopes, accelerometers, etc.) attached either externally or internally. Other applications and functions are also contemplated.

Figure 6:
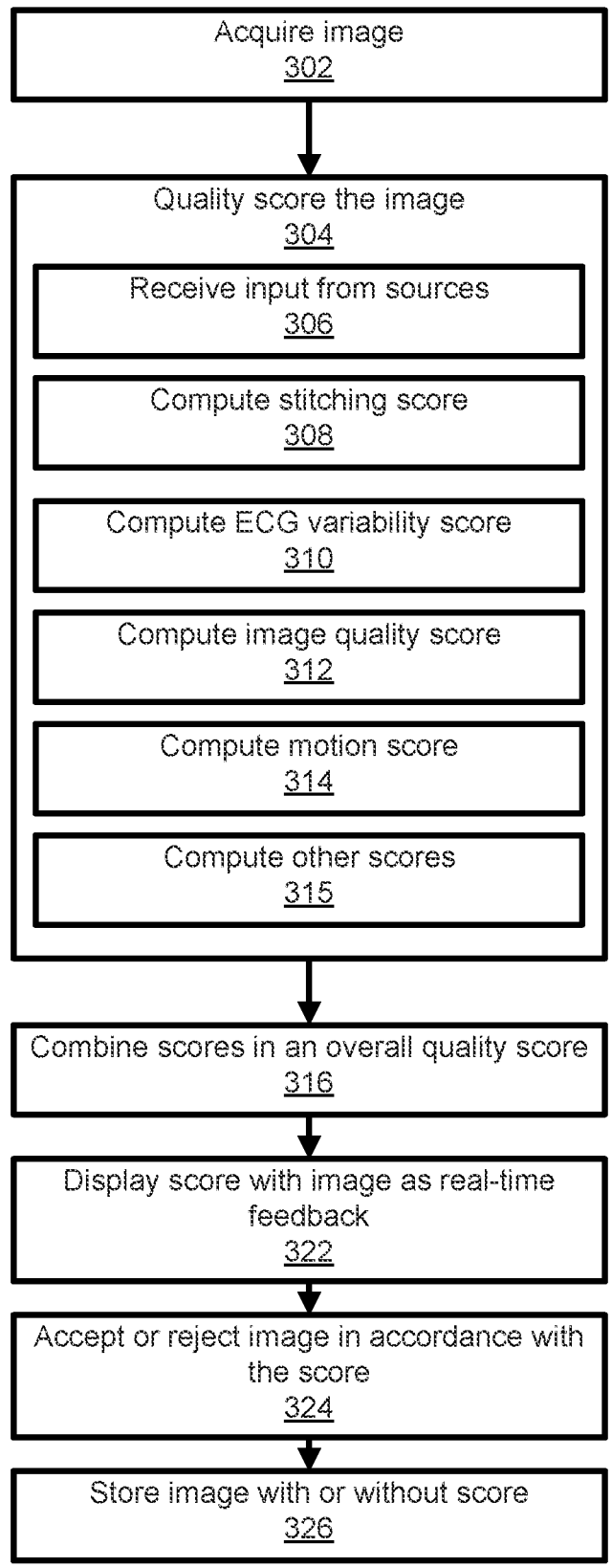
FIG. 6 is a block/flow diagram showing a method for imaging using a quality metric in accordance with illustrative embodiments.

Referring to FIG. 6, an imaging method for acquiring an image in a multi-beat acquisition mode is shown in accordance with the present principles. In block 302, an image is acquired in a multi-beat acquisition mode. In one embodiment, the image includes a multi-beat 3D acquisition image, and, in particular, an apical transthoracic 3D image of a heart. In block 304, the image is quality scored to evaluate changes in the image between portions of a multi-beat cycle. The quality score is computed to indicate suitability of the image.

In block 306, quality scoring may include receiving inputs from one or more sources to evaluate an overall image suitability. The one or more sources may be employed in any combination using the sources described and/or other sources. In block 308, the quality scoring includes computing a stitching score between image stitch locations. In block 310, quality scoring includes computing an electrocardiograph (ECG) variability score between waveforms during a cardiac cycle. In block 312, quality scoring includes computing an image quality score based on scan lines in an image. In block 314, quality scoring includes computing a motion score based upon motion measurements during imaging. In block 315, other quality scores may be computed.

In block 316, individual quality scores may be combined into an overall quality score. In block 322, the image and the quality score are displayed as real-time feedback for the image. In block 324, a user is able to accept or reject the image based on the quality score. In block 326, the image is stored with or without the quality score.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An imaging system, comprising:
   an imaging device configured to acquire imaging data in a multi-beat acquisition mode, wherein the imaging data includes a plurality of portions of a field of view, individual ones of the plurality of portions of the field of view acquired at different beats, and the multi-beat acquisition mode stitches the plurality of portions of the field of view into a single image frame of the field of view;
   a processor;
   a memory configured to receive imaging data corresponding to the single image frame from the imaging device, wherein the memory is further configured to communicate with the processor and includes instructions for causing the processor to:
      compare a first scan line and a second scan line to find a first gradient, wherein the first scan line and the second scan line are from a first portion of the plurality of portions of the field of view in the single image frame;
      compare a third scan line and a fourth scan line to find a second gradient, wherein the third scan line and the fourth scan line are from a second portion of the plurality of portions of the field of view in the single image frame, wherein the second portion of the plurality of portions of the field of view is coupled to the first portion of the plurality of portions of the field of view by a stitch location;
      compare at least one of the first scan line or the second scan line to at least one of the third scan line or the fourth scan line to find a third gradient;
      compare at least one of the first gradient or the second gradient to the third gradient; and
      compute a quality score indicating a suitability of the image generated from the imaging data, based, at least in part, on comparing the third gradient to at least one of the first gradient or the second gradient, wherein the quality score decreases as a difference between the third gradient and the first gradient or the second gradient increases; and
   a display for displaying the image and displaying the quality score corresponding to the image in real-time.

2. The system as recited in claim 1, wherein the memory further includes instructions for receiving inputs from one or more sources other than the imaging data.

3. The system as recited in claim 1, wherein the memory further includes instructions for computing an electrocardiograph (ECG) variability score between waveforms during different cardiac cycles, wherein the quality score is further based, at least in part, on the ECG variability score, wherein the quality score increases when the ECG variability score indicates lower variability between the waveforms and the quality score decreases when the ECG variability score indicates higher variability between the waveforms.

4. The system as recited in claim 1, further comprising an image processor in communication with the imaging device and the imaging data includes acquired scan line data or a mixture of acquired scan line data from the plurality of portions of the field of view and interpolated scan line data, wherein the image processor generates the single image frame from the imaging data and the processor is further configured to determine a proportion of the single image frame generated from acquired scan line data rather than from interpolated scan line data, wherein the quality score is further based, at least in part, on the proportion, wherein the quality score increases as the first proportion increases and the quality score decreases as the first proportion decreases.

5. The system as recited in claim 1, wherein the memory further includes instructions for computing a motion score based upon motion measurements during imaging, wherein the quality score is further based, at least in part, on the motion score, wherein the quality score increases when the motion score indicates less motion and the quality score decreases when the motion score indicates more motion.

6. The system as recited in claim 5, further comprising at least one motion sensor for determining relative motion between the imaging device and a subject being imaged during the multi-beat cycle.

7. The system as recited in claim 1, wherein the imaging device is an ultrasound device.

8. An imaging system, comprising:
   an ultrasound imaging device configured to acquire imaging data in multi-beat acquisition mode, wherein the imaging data includes a plurality of portions of a field of view, individual ones of the plurality of portions of the field of view acquired at different beats, and the multi-beat acquisition mode stitches the plurality of portions of the field of view into a single image frame of the field of view;
   a processor;
   a memory configured to receive imaging data from the ultrasound imaging device, wherein the memory is further configured to communicate with the processor and includes instructions for causing the processor to:
      compare a first scan line and a second scan line to find a first gradient, wherein the first scan line and the second scan line are from a first portion of the plurality of portions of the field of view in the single image frame;
      compare at least one of the first scan line or the second scan line to a third scan line to find a second gradient, wherein the third scan line is from a second portion of the plurality of portions of the field of view in the single image frame, wherein the second portion of the plurality of portions of the field of view is coupled to the first portion of the plurality of portions of the field of view by a stitch location;
      compare the first gradient to the second gradient; and
      compute a quality score indicating a suitability of the image generated from the imaging data, based, at least in part, on comparing the first gradient to the second gradient wherein the quality score decreases as a difference between the first gradient and the second gradient increases;
   a display for displaying the image and displaying the quality score corresponding to the image in real-time; and
   an interface configured to permit acceptance or rejection of the image based on the quality score.

9. The system as recited in claim 8, wherein the memory further includes instructions for accepting inputs from one or more sources other than the imaging data.

10. The system as recited in claim 9, wherein the memory further includes instructions for computing an overall quality score, wherein the overall quality score includes the quality score computed from the first gradient and the second gradient and a quality score computed from the one or more other sources.

11. The system as recited in claim 10, wherein the overall quality score includes a weighted combination of the quality scores.

12. The system as recited in claim 8, further comprising at least one motion sensor for determining relative motion between the imaging device and a subject being imaged during the multi-beat cycle.

13. An imaging method, comprising:
　acquiring imaging data in a multi-beat acquisition mode, wherein the imaging data includes a plurality of portions of a field of view, individual ones of the plurality of portions of the field of view acquired at different beats;
　stitching the plurality of portions of the field of view into a single image frame of the field of view;
　comparing a first scan line and a second scan line to find a first gradient, wherein the first scan line and the second scan line are from a first portion of the plurality of portions of the field of view in the single image frame;
　comparing at least one of the first scan line or the second scan line to a third scan line to find a second gradient, wherein the third scan line is from a second portion of the plurality of portions of the field of view in the single image frame, wherein the second portion of the plurality of portions of the field of view is coupled to the first portion of the plurality of portions of the field of view by a stitch location;
　comparing the first gradient to the second gradient;
　computing a quality score indicating a suitability of the image generated from the imaging data, based, at least in part, on comparing the first gradient to the second gradient, wherein the quality score decreases as a difference between the first gradient and the second gradient increases; and
　displaying the image and the quality score corresponding to the image in real-time.

\* \* \* \* \*